United States Patent [19]

Philpott

[11] Patent Number: 5,125,907
[45] Date of Patent: Jun. 30, 1992

[54] MEDICAL DEVICE
[75] Inventor: Roy A. Philpott, Columbia, S.C.
[73] Assignee: Engitech, Inc., Columbia, S.C.
[21] Appl. No.: 596,195
[22] Filed: Oct. 11, 1990
[51] Int. Cl.$^5$ .................................. A61M 25/02
[52] U.S. Cl. ........................ 640/180; 128/DIG. 26
[58] Field of Search ............... 604/174, 180, 177; 128/DIG. 26

[56] References Cited

U.S. PATENT DOCUMENTS

| | | | |
|---|---|---|---|
| 2,821,194 | 1/1958 | Simmons | 128/214 R |
| 4,275,721 | 6/1981 | Olson | 604/180 |
| 4,324,236 | 4/1982 | Gordon et al. | 604/180 |
| 4,333,468 | 6/1982 | Geist | 604/180 |
| 4,449,975 | 5/1984 | Perry | 604/180 |
| 4,457,754 | 7/1984 | Buttaravoli | 604/180 |
| 4,460,356 | 7/1984 | Moseley | 604/180 |
| 4,484,914 | 11/1984 | Brown | 128/DIG. 26 |
| 4,490,141 | 12/1984 | Lacko et al. | 604/180 |
| 4,534,762 | 8/1985 | Heyer | 604/180 |
| 4,669,458 | 6/1987 | Abraham et al. | 604/180 |
| 4,737,143 | 4/1988 | Russell | 604/180 |
| 4,822,342 | 4/1989 | Brawner | 604/180 |
| 4,898,587 | 2/1990 | Mera | 128/DIG. 26 |
| 4,966,590 | 10/1990 | Kalt | 604/180 |

Primary Examiner—Paul J. Hirsch
Attorney, Agent, or Firm—Dority & Manning

[57] ABSTRACT

A device for securing a portion of a medical appliance in place on a patient for a medical procedure, the device including a first portion for adhesive securement to the skin of a patient and a second portion for holding engagement with a tube. The second portion is associated with the first portion to locate the tube at a predetermined position on the patient. The first portion has at least one non-adhesive surface so that the device can be manipulated without sticking to the fingers or gloves of one applying it.

18 Claims, 1 Drawing Sheet

MEDICAL DEVICE

BACKGROUND OF THE INVENTION

The present invention relates generally to a device for use in medical procedures and, more particularly, to a novel device for securing a portion of a medical appliance such as a tube or the like to a patient during a medical procedure.

During certain medical procedures, it is necessary to rapidly secure a medical appliance such as a tube or the like in place on a patient. The medical appliance must be securely fastened so that it can be maintained in the proper position during the entire procedure. An example of a procedure requiring rapid and secure fastening of a medical appliance would be the application of an endotracheal tube to a patient. The placing and securement of a tube such as an endotracheal tube is complicated by the fact that the personnel securing such tubes are typically wearing gloves which hinder the manipulation of the tube and the securing means.

In the past, the person applying a medical appliance, such as an endotracheal tube, was required to secure it with tape from a conventional roll of tape. This procedure is very difficult because the person placing the tube must maintain it in the proper position while at the same time trying to orient and apply the tape to the patient in a manner that will hold the tube in the desired place. Among the drawbacks of that procedure are the necessity of the person applying the tube having to manipulate the tape from a roll and the problems caused by the conventional tape adhering to the fingers or gloves of the person attempting to secure the tube to the patient.

Thus, many difficulties are encountered in the prior art in attempting to quickly and effectively secure a medical appliance such as a tube or the like to a patient. The present invention recognizes and addresses the foregoing disadvantages, and others, of previously known means of securing medical appliances such as tubes and the like to patients.

SUMMARY OF THE INVENTION

Accordingly, it is an object of the present invention to provide an improved device for securing a medical appliance such as a tube or the like in place on a patient for a medical procedure.

It is another object of the present invention to provide an improved device for securing a medical appliance such as a tube or the like that can be easily handled by personnel without adhering to their fingers or gloves.

It is a further object of the present invention to provide an improved device for securing a medical appliance that can effectively maintain the medical appliance in a predetermined location.

These and other objects are achieved by providing a device for securing a medical appliance in place on a patient for a medical procedure, the device including first means for adhesive securement to the skin of a patient, the first means including a bottom surface and a top surface, the bottom surface having adhesive along at least a portion of the length of same, second means for holding engagement with a medical appliance, the second means being associated with the first means to locate the medical appliance at a predetermined position on the patient, and the first means having at least one non-adhesive portion along the length of the bottom surface so that the device can be manipulated without sticking to the fingers or gloves of one applying the device.

These and other objects of the present invention are also achieved where the first means includes an elongated member with a first and second end, the second means includes an elongated member with a first and second end, and the first end of the second means is unitary with a portion of the first means. The second means may be separable from the first means, and the device may include a plurality of non-adhesive portions located on the bottom surface.

Further, these and other objects may be achieved by providing a device for securing a medical appliance in place on a patient for a medical procedure, the device including a first member with a top and bottom surface, the bottom surface having adhesive along at least a portion of the length of same for adhering to the skin of a patient, a second member for holding engagement with a medical appliance, the second member being unitary with a portion of the first member so that the medical appliance will be held in a desired location when the first member is secured to the patient and the second member is secured to the medical appliance, and a backing for carrying the first and second members prior to use, the backing including portions adapted to be maintained with opposite ends of the first member during use, the portions presenting non-adhesive holding surfaces so that the device can be removed from the backing and placed in a desired location on the skin without adhering to the fingers or gloves of one applying the device.

Other objects, features, and aspects of the present invention are discussed in greater detail below.

BRIEF DESCRIPTION OF THE DRAWINGS

A full and enabling disclosure of the present invention, including the best mode thereof, to one of ordinary skill in the art, is set forth particularly in the remainder of the specification, including reference to the accompanying figures, in which.

Figure 1:
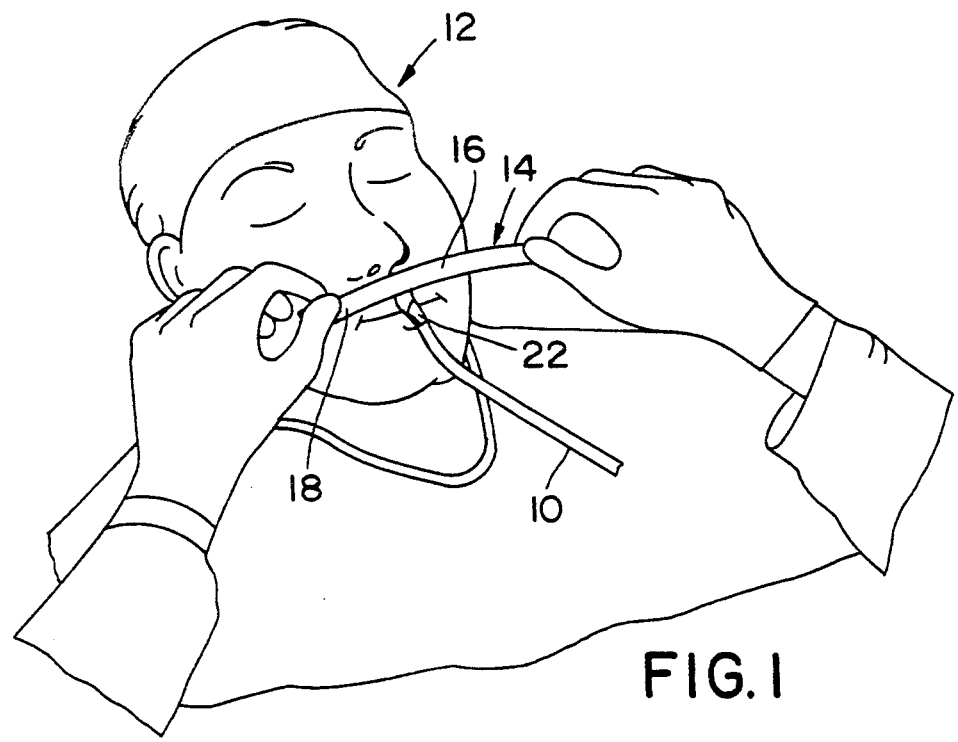
FIG. 1 is an illustration of a device in accordance with the present invention being placed on a patient.

Repeat use of reference characters in the present specification and drawings is intended to represent same or analogous features or elements of the invention.

DESCRIPTION OF THE PREFERRED EMBODIMENTS

Figure 2:
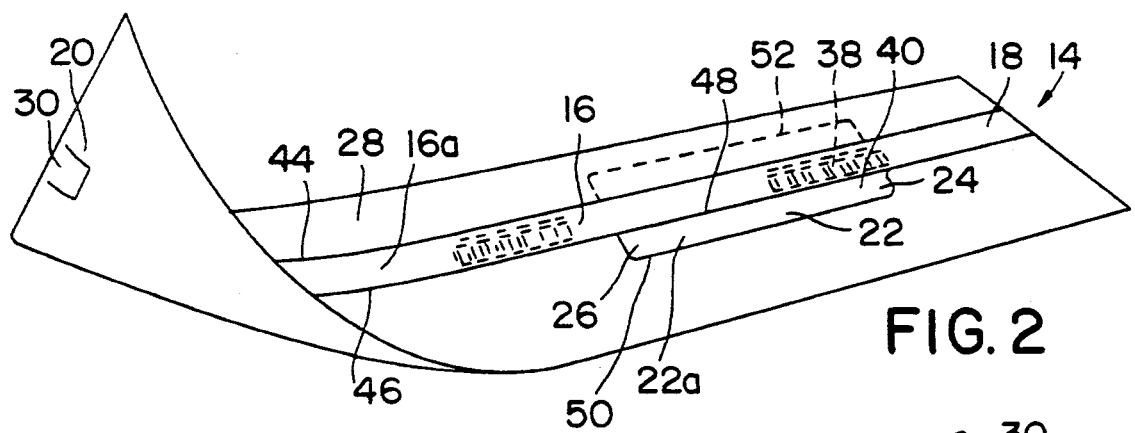
FIG. 2 is a perspective view of the top side of a device as in the present invention with one end turned up to expose the bottom side of the device.

It is to be understood by those of ordinary skill in the art that the present discussion is a description of exemplary embodiments only, and is not intended as limiting the broader aspects of the present invention, which broader aspects are embodied in the exemplary constructions. Referring to FIGS. 1 and 2, a device for securing a medical appliance such as a tube 10 to a patient 12 in accordance with the present invention is generally illustrated at 14. The device includes a first means for adhesive securement to the skin of a patient. As embodied herein, the first means for adhesive securement to the skin includes an elongated member 16 with a first end 18 and a second end 20. Member 16 includes a top surface 16a and a bottom surface 16b (shown in phantom in FIG. 3) and also edges 44 and 46. The bottom surface 16b includes adhesive along at least a portion of its length. In a most preferred embodiment, member 16 may be an elongated strip of adhesive tape.

The device also includes a second means for holding engagement with a medical appliance. As embodied herein, the second means for holding engagement with a medical appliance includes an elongated member or appendage 22 with a first end 24 and a second end 26. Member 22 includes a top surface 22a and a bottom surface 22b (shown in phantom in FIG. 3) and also edges 48 and 50. In a preferred embodiment, member 22 includes adhesive on its bottom surface 22b along at least a portion of its length. In a most preferred embodiment, member 22 may be an elongated strip of adhesive tape. Member 16 is associated with member 22 such that the medical appliance 10 can be held in a predetermined location on the patient 12 when member 16 is secured to the skin as illustrated in FIG. 1. As illustrated in FIG. 1, member 16 can be placed on the patient such as between the nose and mouth if being applied to an endotracheal tube, and member 22 can then be secured to the medical appliance for holding it in place. Of course, the member 22 could be secured to the medical appliance prior to member 16 being placed on the patient.

Preferably, member 16 and member or appendage 22 are unitary at one portion as illustrated for example in FIG. 2 at 40, where first end of member 22 is integral with a portion of member 16. At a portion where members 16 and 22 are not integral, edge 48 is adjacent edge 46 before member 22 is attached to the medical appliance. It is also preferable that member 22 be separable from member 16, that is capable of easily being separated during a medical procedure if necessary or desired. This can be accomplished by utilizing material for members 16 and 22 that is easily tearable at the connection between member 16 and member 22 or by providing perforations or the like between members 16 and 22. In addition, in a preferred embodiment, member 22 is of shorter length than member 16.

Figure 3:
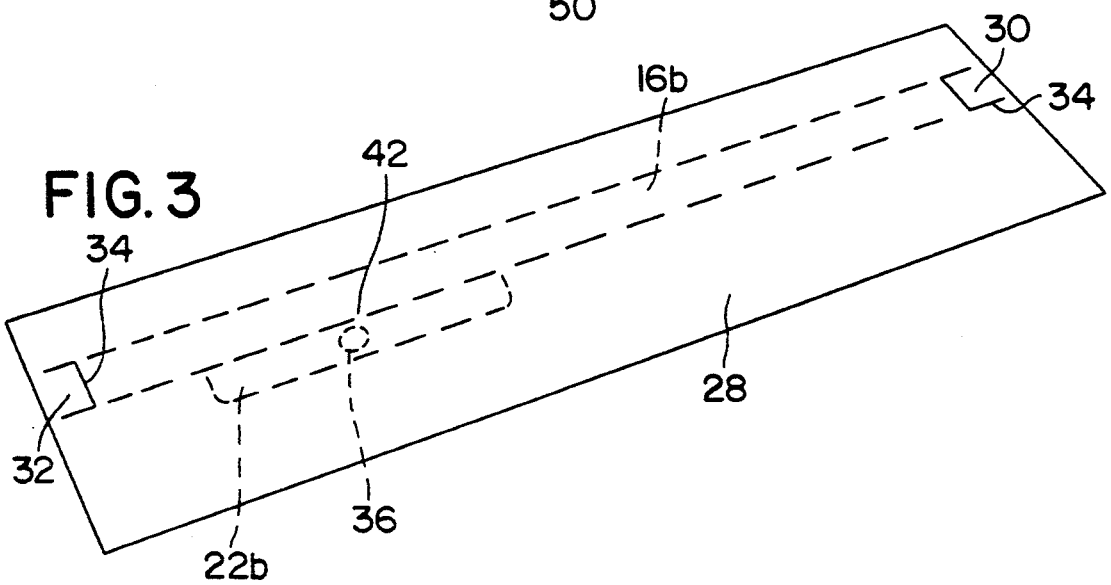
FIG. 3 is a perspective view of the bottom side of a device as in the present invention.

The first means for adhesive securement to the skin includes at least one non-adhesive portion along the length of the bottom surface as illustrated at 30 or 32 so that the device can be manipulated without sticking to the fingers or gloves of one applying the device. As defined herein, a non-adhesive portion can include a portion where there is no adhesive or a portion where there is adhesive, but it is masked in some way to present a non-adhesive surface for holding. As illustrated in FIGS. 2 and 3, the device 14 preferably includes a backing 28 for carrying members 16 and 22. The backing 28 preferably is a paper type material that allows the members 16 and 22 to adhere to it and allows them to be easily removed for application to the patient. An example of such a material would be a paper with a coating on a surface for receiving the members so that the device can be easily released from the paper for application to the patient.

As illustrated in FIGS. 2 and 3, backing 28 includes holding portions 30 and 32 adapted to be maintained with opposite ends of the first elongated member 16 during use. The holding portions 30 and 32 are defined by slits 34 in the backing 28 which allow the portions 30 and 32 to be detached from the remainder of the backing 28 when members 16 and 22 are removed from the backing 28 for application to a patient. As a result, member 16, to which member 22 is unitary with or attached, is removed from the backing by grasping it at its first and second ends 18 and 20 where the holding portions 30 and 32 are located. The holding portions 30 and 32 break away from the backing 28 when the members 16 and 22 are removed from the backing and remain with the opposite ends of member 16 thereby providing non-adhesive surfaces for manipulating the device which do not adhere to the fingers or gloves of the person using the device. Further since the non-adhesive holding portions remain with member 16, they can be used to remove the device from the patient's skin in the same manner as when the device is applied, thus preventing the strips from sticking to the user's hands or gloves during removal. Alternatively, the non-adhesive holding portions can be removed for full adhesive engagement of member 16 with the patient.

It should be understood that any manner of producing non-adhesive surfaces on the members so that they can be manipulated without sticking to the user's fingers or gloves is within the scope of the present invention. Such would include, for example, provision of a portion of the member for holding that is without any adhesive. In addition, portions 30 and 32 could be padded to provide a contrast to the other portions of the member 16 to enhance the ability to grasp the portions for the person applying the device.

As set forth above, in a preferred embodiment, the first end 24 of member 22 is integral with a portion of member 16. However, it is also within the scope of this invention for the member 22 to be integral at any portion therealong with member 16 such as for example on second end 20 or in a medial portion 42 as illustrated in phantom in FIG. 3. In addition, while it is preferred that member 22 have adhesive along at least a portion of a bottom surface, it is also within the scope of this invention for member 22 to be non-adhesive and define a hole or slot 36 therein as illustrated in phantom in FIG. 3 for receipt of the medical appliance 10. In addition, any means of securing the medical appliance to the member 22 would be within the scope of this invention.

It is preferred that members 16 and 22 are made of medical specialty tape such as a polyvinyl tape which has the characteristics of adhering well to the skin and being removable without pulling or causing discomfort to the patient and without leaving adhesive residue on the skin. One tape of this type is sold by the Avery Tape Company under the designation Med. 5502. It is also within the scope of this invention to utilize any type tape or material for the members 16 and 22 that will securely hold the tube in place on the patient. The material used for the members 16 and 22 may be of a type that can carry advertising or other printed material thereon such as illustrated at in FIG. 2.

Preferably, member 16 is approximately 9 (nine) inches in length and ⅝ (five eighths) of an inch in width. Member 22 is preferably approximately 3 (three) inches in length and ½ (one half) inch in width. Backing 28 is preferably approximately 9 (nine) inches in length and three (3) inches in width. Of course, variations from the above dimensions would be well within the scope of this invention including variation of the length of member 22 with respect to member 16. In a most preferred embodiment, members 16 and 22 are unitary, i.e., made from the same larger strip of material such as by die cutting. It is also within the scope of the present invention for members 16 and 22 to be integral or attached instead of unitary. Further, an additional member or appendage on the opposite side of member 16 could be utilized such as illustrated in phantom in FIG. 2 as 52. It should also be understood that this device can be used to secure different types of medical appliances in place for various medical procedures such as, for example, tube feeding of a patient, securing an airway in place in an emergency, or securement of a needle in place. In addition, as utilized herein, the word "medical" should be broadly construed and is not limited to humans but is considered to include procedures involving animals as well.

These and other modifications and variations to the present invention may be practiced by those of ordinary skill in the art, without departing from the spirit and scope of the present invention, which is more particularly set forth in the appended claims. The various embodiments set forth can be interchanged both in whole or in part. Furthermore, those of ordinary skill in the art will appreciate that the foregoing description is by way of example only, and is not intended to be limitative of the invention so further described in such appended claims.

What is claimed is:

1. A device for securing a medical appliance in place on a patient for a medical procedure, said device comprising:

first means for adhesive securement to the skin of a patient, said first means comprising an elongated member with a first and second end, said first means including a bottom surface, a top surface, and two side edges, said bottom surface having adhesive along at least a portion of the length of same;

second means for holding engagement with a medical appliance, said second means comprising an elongated member with a first and second end, a bottom surface, a top surface and two side edges, one edge of said second means being located substantially parallel to and adjacent one edge of said first means prior to use, said second means including adhesive along at least a portion of its bottom surface and being attached to said first means to locate said medical appliance at a predetermined position on said patient during use; and said first means having at least one non-adhesive portion along the length of the bottom surface so that the device can be manipulated without sticking to the fingers or gloves of one applying the device.

2. A device as in claim 1, wherein
said first end of said second means is unitary with a portion of said first means.

3. A device as in claim 2, wherein said second means is separable from said first means.

4. A device as in claim 1 and further including a plurality of non-adhesive portions located on said bottom surface.

5. A device as in claim 2 and further including a non-adhesive portion on each end of the bottom surface of the first means.

6. A device as in claim 2, wherein said first and second means are polymeric tape adapted to adhesively adhere to the skin and be removed without leaving a residue.

7. A device for securing a medical appliance in place on a patient for a medical procedure, said device comprising:

(a) a first member with a top and bottom surface, said bottom surface having adhesive along at least a portion of the length of same for adhering to the skin of a patient;

(b) a second member for holding engagement with a medical appliance, said second member being unitary with a portion of said first member so that the medical appliance will be held in a desired location when the first member is secured to the patient and the second member is secured to the medical appliance;

(c) a backing for carrying said first and second members prior to use, said backing including portions adapted to be maintained with opposite ends of the first member during use, said portions presenting non-adhesive holding surfaces so that the device can be removed from the backing and placed in a desired location on the skin without adhering to the fingers or gloves of one applying the device.

8. A device as in claim 7, wherein said first member has a first and second end;
   said second member has a first and second end; and
   wherein the first end of said second member is unitary with said first member.

9. A device as in claim 8, wherein said first and second members are separably attached.

10. A device as in claim 7, wherein said first member is polyvinyl tape adapted to releasably adhere to the skin.

11. A device as in claim 10, wherein said second member is polyvinyl tape adapted to adhere to a tube.

12. A device as in claim 7, wherein said first and second members are elongated.

13. A device for securing a medical appliance in place on a patient for a medical procedure comprising:

a flexible member having a bottom surface and a top surface, said bottom surface having adhesive along a portion of the length of same for securement of said device to a patient, said member further having non-adhesive portions along said bottom surface to facilitate handling without sticking to a handler during placement of the device;

an appendage secured to said flexible member along at least a portion of an edge of same and extending in the same plane as said flexible member, said appendage having a bottom surface and a top surface, said appendage having means thereon for holding engagement with a medical appliance, said means for holding engagement including adhesive along at least a portion of the bottom surface of said appendage.

14. A device as defined in claim 13 wherein said flexible member and said appendage are elongated and wherein said appendage is unitary with said flexible member along a portion thereof.

15. A device as defined in claim 14 wherein said elongated appendage is a strip secured to said flexible member along a medial portion of the appendage and is separate therefrom on opposite sides of said medial portion.

16. A device as defined in claim 13 wherein said elongated appendage is a strip secured to said flexible member at an end portion of the appendage and is separate therefrom on an end opposite the secured end.

17. A device as defined in claim 13 and further including a second appendage secured to said flexible member.

18. A device for securing a medical appliance in place on a patient for a medical procedure, said device comprising:

a first member for adhesive securement to the skin of a patient, said first member comprising an elongated strip of medical grade tape and including a bottom surface, a top surface, and two side edges, said bottom surface having adhesive along a portion of the length of same;

a second member for holding engagement with a medical appliance, said second member comprising an elongated strip of medical grade tape and including a bottom surface, a top surface and two side edges, at least a portion of one edge of said second member being located substantially parallel to, in the same plane as, and adjacent at least a portion of one edge of said first member prior to use, said second member including a portion integral with said first member at an end portion of said second member and a portion separate therefrom on an opposite end, said second member including adhesive along at least a portion of its bottom surface so as to locate said medical appliance at a predetermined position on said patient during use; and said first member having a non-adhesive portion on the bottom surface of each end thereof so that the device can be manipulated without sticking to the fingers or gloves of one applying the device.

* * * * *